United States Patent
Lin et al.

(10) Patent No.: US 8,653,332 B2
(45) Date of Patent: Feb. 18, 2014

(54) EXTRACELLULAR PLANT FERREDOXIN-LIKE PROTEIN AND USES THEREOF

(75) Inventors: Yi-Hsien Lin, Taipei (TW); Hsiang-En Huang, Taitung (TW); Teng-Yung Feng, Taipei (TW)

(73) Assignee: Academia Sinica, Taipei (TW)

( * ) Notice: Subject to any disclaimer, the term of this patent is extended or adjusted under 35 U.S.C. 154(b) by 6 days.

(21) Appl. No.: 13/321,691

(22) PCT Filed: May 24, 2010

(86) PCT No.: PCT/US2010/035910
§ 371 (c)(1),
(2), (4) Date: Feb. 2, 2012

(87) PCT Pub. No.: WO2010/135728
PCT Pub. Date: Nov. 25, 2010

(65) Prior Publication Data
US 2012/0144534 A1   Jun. 7, 2012

Related U.S. Application Data

(60) Provisional application No. 61/180,563, filed on May 22, 2009.

(51) Int. Cl.
*C12N 15/82* (2006.01)
*A01N 63/00* (2006.01)
*C12N 15/00* (2006.01)

(52) U.S. Cl.
USPC ......... 800/301; 424/93.2; 536/23.4; 930/230; 435/320.1

(58) Field of Classification Search
None
See application file for complete search history.

(56) References Cited

U.S. PATENT DOCUMENTS 6,566,588 B1 *  5/2003  Feng et al. .................. 800/301
6,861,578 B1    3/2005  Jongsma et al.

FOREIGN PATENT DOCUMENTS

WO        WO 9858068 A2 * 12/1998

OTHER PUBLICATIONS

Guo et al. 2004. Protein tolerance to random amino acid change. PNAS. 101(25):9205-9210.*
Dayakar et al.; Plant Mol. Biol., 51(6):913-924 (2003) "Ferredoxin from sweet pepper intensifying harpin (pss)-mediated hypersensitive response shows and enhanced production of active oxygen species (AOS)".

* cited by examiner

*Primary Examiner* — Anne Kubelik
*Assistant Examiner* — Jeffrey Bolland
(74) *Attorney, Agent, or Firm* — Cesari and McKenna, LLP

(57) ABSTRACT

Disclosed are polypeptides, nucleic acids, and related compositions that render plants resistant to bacterial pathogens. Also disclosed are transgenic plants having the nucleic acids and resistant to bacterial pathogens.

16 Claims, 7 Drawing Sheets

SEQUENCE LISTING

```
<160> NUMBER OF SEQ ID NOS: 19

<210> SEQ ID NO 1
<211> LENGTH: 144
<212> TYPE: PRT
<213> ORGANISM: Artificial sequence
<220> FEATURE:
<223> OTHER INFORMATION: Synthetic polypeptide

<400> SEQUENCE: 1

Met Ala Ser Val Ser Ala Thr Met Ile Ser Thr Ser Phe Met Pro Arg
1               5                   10                  15

Lys Pro Ala Val Thr Ser Leu Lys Pro Ile Pro Asn Val Gly Glu Ala
            20                  25                  30

Leu Phe Gly Leu Lys Ser Ala Asn Gly Gly Lys Val Thr Cys Met Ala
        35                  40                  45

Ser Tyr Lys Val Lys Leu Ile Thr Pro Asp Gly Pro Ile Glu Phe Asp
    50                  55                  60

Cys Pro Asp Asn Val Tyr Ile Leu Asp Gln Ala Glu Glu Ala Gly His
65                  70                  75                  80

Asp Leu Pro Tyr Ser Cys Arg Ala Gly Ser Cys Ser Ser Cys Ala Gly
                85                  90                  95

Lys Ile Ala Gly Gly Ala Val Asp Gln Thr Asp Gly Asn Phe Leu Asp
            100                 105                 110

Asp Asp Gln Leu Glu Glu Gly Trp Val Leu Thr Cys Val Ala Tyr Pro
        115                 120                 125

Gln Ser Asp Val Thr Ile Glu Thr His Lys Glu Ala Glu Leu Val Gly
    130                 135                 140
```

<210> SEQ ID NO 2
<211> LENGTH: 435
<212> TYPE: DNA
<213> ORGANISM: Artificial sequence
<220> FEATURE:
<223> OTHER INFORMATION: Synthetic polynucleotide

<400> SEQUENCE: 2

```
atggctagtg tctcagctac catgattagt acctccttca tgccaagaaa accagctgtg      60
acaagcctta acccatccc aaacgttggg gaagcactgt ttgggcttaa atcagcaaat     120
ggtggcaaag tcacttgcat ggcttcatac aaagtgaaac ttatcacacc tgacggacca     180
atagaatttg attgcccaga taatgtgtac attcttgatc aagctgagga agcaggacat     240
gatcttcctt attcgtgcag ggcaggttct tgctcatctt gtgctggtaa aattgctggt     300
ggagctgttg atcaaactga tggcaacttt cttgatgatg accaattaga ggagggatgg     360
gtgctaactt gtgttgctta tccacagtct gatgttacta ttgagactca caaagaggca     420
gaactcgtgg gctaa                                                     435
```

<210> SEQ ID NO 3
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 3

```
Met Ala Ser Val Ser Ala Thr Met Ile Ser Thr Ser Phe Met Pro Arg
1               5                   10                  15

Lys Pro Ala Val Thr Ser Leu Lys Pro Ile Pro Asn Val Gly Glu Ala
            20                  25                  30

Leu Phe Gly Leu Lys Ser Ala Asn Gly Gly Lys Val Thr Cys
        35                  40                  45
```

<210> SEQ ID NO 4
<211> LENGTH: 114
<212> TYPE: DNA
<213> ORGANISM: Artificial sequence
<220> FEATURE:
<223> OTHER INFORMATION: Synthetic polynucleotide

<400> SEQUENCE: 4

```
attagtacct ccttcatgcc aagaaaacca gctgtgacaa gccttaaacc catcccaaac      60
gttggggaag cactgtttgg gcttaaatca gcaaatggtg gcaaagtcac ttgc            114
```

<210> SEQ ID NO 5
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 5

```
Met Ala Ser Tyr Lys Val Lys Leu Ile Thr Pro Asp Gly Pro Ile Glu
1               5                   10                  15

Phe Asp Cys Pro Asp Asn Val Tyr Ile Leu Asp Gln Ala Glu Glu Ala
            20                  25                  30

Gly His Asp Leu Pro Tyr Ser Cys Arg Ala Gly Ser Cys Ser Ser Cys
        35                  40                  45

Ala Gly Lys Ile Ala Gly Gly Ala Val Asp Gln Thr Asp Gly Asn Phe
```

```
                50                  55                  60
Leu Asp Asp Gln Leu Glu Glu Gly Trp Val Leu Thr Cys Val Ala
 65                  70                  75                  80

Tyr Pro Gln Ser Asp Val Thr Ile Glu Thr His Lys Glu Ala Glu Leu
                 85                  90                  95

Val Gly

<210> SEQ ID NO 6
<211> LENGTH: 297
<212> TYPE: DNA
<213> ORGANISM: Artificial sequence
<220> FEATURE:
<223> OTHER INFORMATION: Synthetic polynucleotide

<400> SEQUENCE: 6
atggcttcat acaaagtgaa acttatcaca cctgacggac caatagaatt tgattgccca      60
gataatgtgt acattcttga tcaagctgag gaagcaggac atgatcttcc ttattcgtgc     120
agggcaggtt cttgctcatc ttgtgctggt aaaattgctg gtggagctgt tgatcaaact     180
gatggcaact tccttgatga tgaccaatta gaggagggat gggtgctaac ttgtgttgct     240
tatccacagt ctgatgttac tattgagact cacaaagagg cagaactcgt gggctaa       297

<210> SEQ ID NO 7
<211> LENGTH: 136
<212> TYPE: PRT
<213> ORGANISM: Artificial sequence
<220> FEATURE:
<223> OTHER INFORMATION: Synthetic polypeptide

<400> SEQUENCE: 7

Met Ser Leu Ser Gln Asn Gln Ala Lys Phe Ser Lys Gly Phe Val Val
 1               5                  10                  15

Met Ile Trp Val Leu Phe Ile Ala Cys Ala Ile Thr Ser Thr Glu Ala
                20                  25                  30

Ser Pro Met Asp Pro Arg Met Ala Ser Tyr Lys Val Lys Leu Ile Thr
             35                  40                  45

Pro Asp Gly Pro Ile Glu Phe Asp Cys Pro Asp Asp Val Tyr Ile Leu
 50                  55                  60

Asp Gln Ala Glu Glu Ala Gly His Asp Leu Pro Tyr Ser Cys Arg Ala
 65                  70                  75                  80

Gly Ser Cys Ser Ser Cys Ala Gly Lys Ile Ala Gly Gly Ala Val Asp
                 85                  90                  95

Gln Thr Asp Gly Asn Phe Leu Asp Asp Gln Leu Glu Glu Gly Trp
            100                 105                 110

Val Leu Thr Cys Val Ala Tyr Pro Gln Ser Asp Val Thr Ile Glu Thr
        115                 120                 125

His Lys Glu Ala Glu Leu Val Gly
    130                 135

<210> SEQ ID NO 8
<211> LENGTH: 427
<212> TYPE: DNA
<213> ORGANISM: Artificial sequence
<220> FEATURE:
<223> OTHER INFORMATION: Synthetic polynucleotide

<400> SEQUENCE: 8
atgtctctta gccagaacca ggccaagttt tccaagggat cgtcgtgat gatttgggta      60 ctattcattg cttgtgctat cacttcaact gaagctagtc ccatggatcc gcgcatggct    120
```

```
tcatacaaag tgaaacttat cacacctgac ggaccaatag aatttgattg cccagatgat      180
gtgtacattc ttgatcaagc tgaggaagca ggacatgatc ttccttattc gtgcagggca      240
ggttcttgct catcttgtgc tggtaaaatt gctggtggag ctgttgatca aactgatggc      300
aactttcttg atgatgacca attagaggag ggatgggtgc taacttgtgt tgcttatcca      360
cagtctgatg ttactattga gactcacaaa gaagcagaac tcgtgggcta aggaagatct      420
ccaataa                                                                427
```

<210> SEQ ID NO 9
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 9

Met Ser Leu Ser Gln Asn Gln Ala Lys Phe Ser Lys Gly Phe Val Val
1               5                   10                  15

Met Ile Trp Val Leu Phe Ile Ala Cys Ala Ile Thr Ser Thr Glu Ala
            20                  25                  30

Ser Pro Met Asp Pro Arg
        35

<210> SEQ ID NO 10
<211> LENGTH: 114
<212> TYPE: DNA
<213> ORGANISM: Artificial sequence
<220> FEATURE:
<223> OTHER INFORMATION: Synthetic polynucleotide

<400> SEQUENCE: 10
atgtctctta gccagaacca ggccaagttt tccaagggat cgtcgtgat gatttgggta       60 ctattcattg cttgtgctat cacttcaact gaagctagtc ccatggatcc gcgc           114

<210> SEQ ID NO 11
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 11

Met Ala Ser Tyr Lys Val Lys Leu Ile Thr Pro Asp Gly Pro Ile Glu
1               5                   10                  15

Phe Asp Cys Pro Asp Asp Val Tyr Ile Leu Asp Gln Ala Glu Glu Ala
            20                  25                  30

Gly His Asp Leu Pro Tyr Ser Cys Arg Ala Gly Ser Cys Ser Ser Cys
        35                  40                  45

Ala Gly Lys Ile Ala Gly Gly Ala Val Asp Gln Thr Asp Gly Asn Phe
    50                  55                  60

Leu Asp Asp Asp Gln Leu Glu Glu Gly Trp Val Leu Thr Cys Val Ala
65                  70                  75                  80

Tyr Pro Gln Ser Asp Val Thr Ile Glu Thr His Lys Glu Ala Glu Leu
                85                  90                  95

Val Gly

<210> SEQ ID NO 12
<211> LENGTH: 313
<212> TYPE: DNA

<213> ORGANISM: Artificial sequence
<220> FEATURE:
<223> OTHER INFORMATION: Synthetic polynucleotide

<400> SEQUENCE: 12

```
atggcttcat acaaagtgaa acttatcaca cctgacggac caatagaatt tgattgccca    60
gatgatgtgt acattcttga tcaagctgag gaagcaggac atgatcttcc ttattcgtgc   120
agggcaggtt cttgctcatc ttgtgctggt aaaattgctg gtggagctgt tgatcaaact   180
gatggcaact ttcttgatga tgaccaatta gaggagggat gggtgctaac ttgtgttgct   240
tatccacagt ctgatgttac tattgagact cacaaagaag cagaactcgt gggctaagga   300
agatctccaa taa                                                      313
```

<210> SEQ ID NO 13
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 13

```
cgcggatccg cgcatggctt catacaaagt g                                   31
```

<210> SEQ ID NO 14
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 14

```
ccatcgggct tatgagatca gagctc                                         26
```

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15

```
tctagaatgg cctcgatctc                                                20
```

<210> SEQ ID NO 16
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 16

```
tctagaaacc atgtctctta gccagaac                                       28
```

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17

```
cccagtcacg acgttgtaaa                                                20
```

<210> SEQ ID NO 18

-continued

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 18
cacacctgac ggaccaat                                            18

<210> SEQ ID NO 19
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 19
cgagttctgc ttctttgtg                                           19
```

EXTRACELLULAR PLANT FERREDOXIN-LIKE PROTEIN AND USES THEREOF

RELATED APPLICATION

This application is the National Stage of International Application No. PCT/US2010/35910, filed on May 24, 2010, which claims priority to U.S. Provisional Application No. 61/180,563, filed on May 22, 2009, the content of which is hereby incorporated by reference in its entirety.

BACKGROUND

Plant ferredoxin-like protein (PFLP), a photosynthetic type ferredoxin, is a protein associated with the production of active oxygen species and hypersensitive reaction in plants. Over-expression of PFLP renders plants resistant to bacterial pathogens. However, such a resistance is still not sufficient. There is a need for a further enhanced resistance.

SUMMARY

This invention relates to a mutant form of PFLP that enhances plants' resistant to bacterial pathogens. Shown below is the sequence of the full length wild type PFLP (SEQ ID NO: 1) and the nucleotide sequence encoding it (SEQ ID NO: 2).

```
                                             (SEQ ID NO: 1)
MASVSATMISTSFMPRKPAVTSLKPIPNVGEALFGLKSANGGKVTC

MASYKVKLITPDGPIEFDCPDNVYILDQAEEAGHDLPYSCRAGSCS

SCAGKIAGGAVDQTDGNFLDDDQLEEGWVLTCVAYPQSDVTIETHK

EAELVG
```

```
                                             (SEQ ID NO: 2)
atggctagtgtctcagctaccatgattagtacctccttcatgccaa gaaaaccagctgtgacaagccttaaacccatcccaaacgttgggga agcactgtttgggcttaaatcagcaaatggtggcaaagtcacttgc atggcttcatacaaagtgaaacttatcacacctgacggaccaatag aatttgattgcccagataatgtgtacattcttgatcaagctgagga agcaggacatgatcttccttattcgtgcagggcaggttcttgctcat cttgtgctggtaaaattgctggtggagctgttgatcaaactgatgg caactttcttgatgatgaccaattagaggagggatgggtgctaact tgtgttgcttatccacagtctgatgttactattgagactcacaaag aggcagaactcgtgggctaa
```

The above PFLP has a chloroplast targeting signal polypeptide (csp) sequence. This csp sequence and corresponding nucleotide sequences are: MASVSATMISTSFMPRK-PAVTSLKPIPNVGEALFGLKSANGGKVTC (SEQ ID NO: 3) and atggctagtgtctcagctaccatg attagtacctccttcatgccaa-gaaaaccagctgtgacaagccttaaacccatcccaaacgttggggaagcactg tttgggcttaaatcagcaaatggtggcaaagtcacttgc (SEQ ID NO:4). The underlined sequences are those that lack the csp, i.e., d-pflp polypeptide and coding sequences (SEQ ID NOs: 5 and 6, respectively).

One aspect of this invention features an isolated, fusion polypeptide comprising a first segment that contains SEQ ID NO: 5, and a second segment that contains the sequence of an extracellular secretion signal polypeptide (esp). The polypeptide can be one from a plant, such as a cotton, pepper, tobacco, or tomato plant. Once present in a plant, the above-described polypeptide enhances disease resistance of the plant against a bacterial pathogen. Examples of the pathogen include *Xanthomonas oryzae* pv. *oryzae*, *Erwinia carotovora* subsp. *carotovora*, *Ralstonia solanacearum*. Examples of diseases caused by these pathogens include bacterial leaf blight in rice, bacterial soft rot in tobacco, tomato, calla lily and orchid, and bacterial wilt in tomato.

The sequence of the extracellular secretion signal polypeptide can be one from any secreted protein. For example, the extracellular secretion signal polypeptide can be an esp sequence from sea anemone, such as MSLSQNQAKFSKG-FVVMIWVLFIACAITSTEASPMDPR (SEQ ID NO: 9), which can be encoded by atgtctcttagccagaaccaggc-caagtlttccaagggattcgtcgtgatgatttgggtactattcattgctt gtgctat-cacttcaactgaagctagtcccatggatccgcgc (SEQ ID NO: 10). Shown below are the sequence of an exemplary fusion polypeptide, espflp and its encoding nucleic acid sequence, i.e., SEQ ID NOs: 7 and 8, respectively:

```
                                             (SEQ ID NO: 7)
MSLSQNQAKFSKGFVVMIWVLFIACAITSTEASPMDPRMASYKVK

LITPDGPIEFDCPDDVYILDQAEEAGHDLPYSCRAGSCSSCAGKI

AGGAVDQTDGNFLDDDQLEEGWVLTCVAYPQSDVTIETHKEAELV

G
```

```
                                             (SEQ ID NO: 8)
atgtctcttagccagaaccaggccaagttttccaagggattcgtc gtgatgatttgggtactattcattgcttgtgctatcacttcaact gaagctagtcccatggatccgcgcatggcttcatacaaagtgaaa cttatcacacctgacggaccaatagaatttgattgcccagatgat gtgtacattcttgatcaagctgaggaagcaggacatgatcttcct tattcgtgcagggcaggttcttgctcatcttgtgctggtaaaatt gctggtggagctgttgatcaaactgatggcaactttcttgatgat gaccaattagaggagggatgggtgctaacttgtgttgcttatcca cagtctgatgttactattgagactcacaaagaagcagaactcgtg ggctaaggaagatctccaataa
```

Examples of the above-described polypeptide also include one encoded by a nucleic acid that, under a stringent condition, hybridize to the compliment of a reference nucleic acid consisting of SEQ ID NO: 6 or 8.

The underlined sequences are the polypeptide and coding sequences (SEQ ID NOs: 11 and 12, respectively) of es-pflp that lacks the extracellular secretion signal.

An "isolated polypeptide" refers to a polypeptide that has been separated from other proteins, lipids, and nucleic acids with which it is naturally associated. It can be a preparation that contains at least 10% (i.e., any number between 10% and 100%, inclusive) by dry weight the pure polypeptide. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods.

The invention also features an isolated nucleic acid that contains a sequence encoding one of the above-mentioned polypeptides or a complement thereof. Examples of the nucleic acid include those having SEQ ID NO: 8 as well as those that are at least 70% (e.g., 75%, 80%, 85%, 90%, 95%, 99%, or 100%) identical to SEQ ID NO: 8. Examples also include a nucleic acid that hybridizes to the compliment of a reference nucleic acid consisting of SEQ ID NO: 6 or 8 under a stringent condition. This nucleic acid encodes a polypeptide that is expressed extracellularly in a plant and the presence of the polypeptide in the plant enhances disease resistance of the plant against a bacterial pathogen. Such an isolated nucleic acid can encode a polypeptide having an amino acid sequence at least 70-99% identical to SEQ ID NO:7.

The "percent identity" of two amino acid sequences or of two nucleic acids is determined using the algorithm of Karlin and Altschul *Proc. Natl. Acad. Sci.* USA 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength—12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized in the manner described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Stringent hybridization conditions for obtaining nucleic acids encoding functionally equivalent proteins of the above-described polypeptide can be suitably selected by one skilled in the art, and for example, low-stringent conditions can be given. Low-stringent conditions are, for example, 42° C., 2×SSC, and 0.1% SDS, and preferably, 50° C., 2×SSC, and 0.1% SDS. Highly stringent conditions are more preferable and include, for example, 65° C., 2×SSC, and 0.1% SDS. Under these conditions, the higher the temperature, the higher the homology of the obtained nucleic acids will be. However, several factors other than temperature, such as salt concentration, can influence the stringency of hybridization and one skilled in the art can suitably select the factors to accomplish a similar stringency.

A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express a polypeptide of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention.

Also within the scope of this invention is a host cell that contains the above-described nucleic acid. Examples include *E. coli* cells, insect cells (e.g., using baculovirus expression vectors), yeast cells, plant cells, or mammalian cells. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

In another aspect, this invention features a transformed cell containing a heterologous polynucleotide containing a nucleic acid encoding one of the above-described polypeptides. The transformed cell can be made by conventional methods and used to generate a transgenic plant whose genome comprises a heterologous polynucleotide containing the nucleic acid. Transgenic plants thus-generated express the above-described polypeptide extracellularly and are resistant to various plant pathogens, such as a bacterial pathogen, including a pathogenic Gram-negative bacterium.

A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid. In preferred examples, the transgenic plants have genomic DNA comprises the above-described nucleic acids.

The above-described polypeptide can be used in a composition, e.g., a composition which includes agriculturally acceptable carriers, or other agents, to protect plants from pathogens, insects, and other pests. The composition can be formulated and applied by methods described herein or those known in the art protect a plant.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
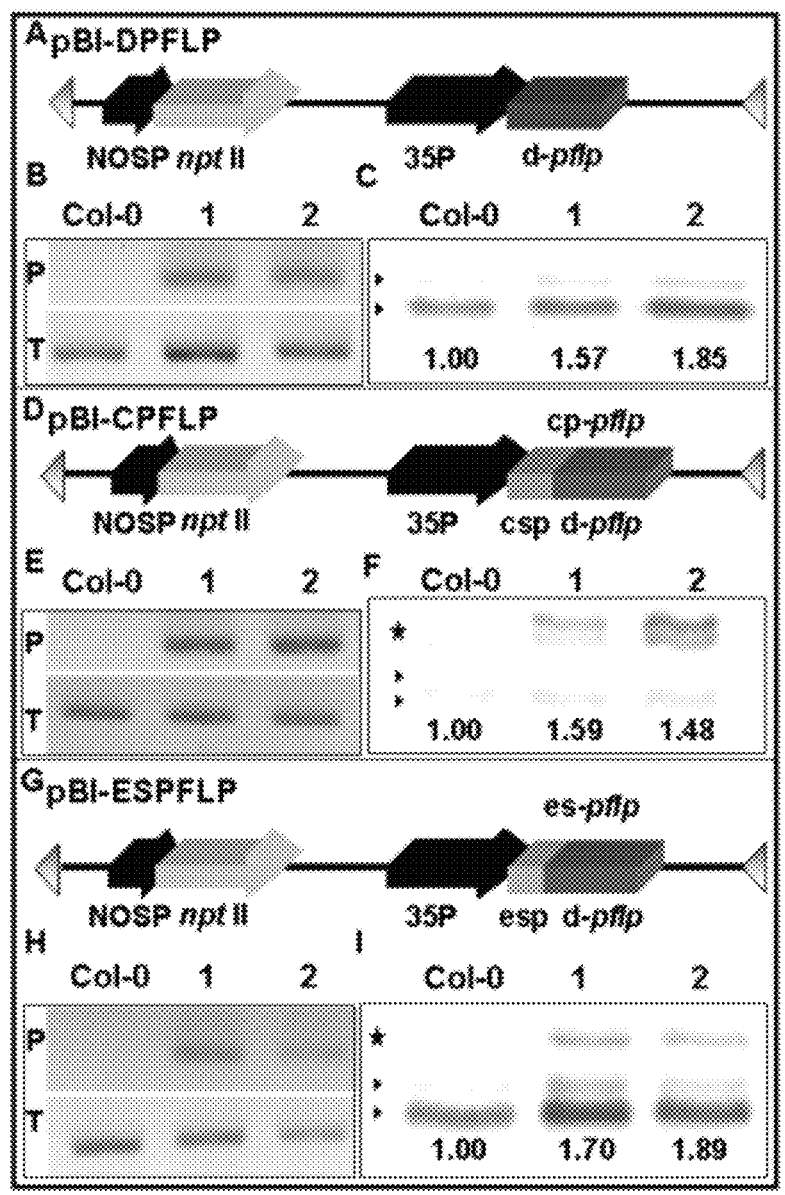
FIG. 1 is a set of diagrams and photographs showing expression constructs and related Western blot results. Panels A, D and G: Schematic diagrams that depict the T-DNA region in plasmids pBID-PFLP, pBIC-PFLP and pBIES-PFLP harbouring d-pflp, cp-pflp and es-pflp fragments, respectively. NOS promoter (NOSP) was used to drive kanamycin resistance gene (nptII) as a selection maker for transformation, and CaMV 35S promoter (35P) was used to drive the target gene (d-pflp) or d-pflp in-frame fused to a signal peptide sequence (csp or esp) for chloroplast targeting or extracellular secretion. Panels B, E and H: RT-PCR revealed the presence of mRNA transcripts of two transgenic *Arabidopsis* lines AtDPFLP (1: line #1-8; 2: line #6-7), AtCPFLP (1: line #2-1; 2: line #11-3) and AtESPFLP (1: line #1-19, 2: line #2-9) containing d-pflp, cp-pflp and es-pflp constructs, respectively. Letter P in the upper panels of B, E and H shows the presence of a 0.25 Kb band of the pflp gene. Letter T in the lower panels indicates the presence of a 0.5 Kb band for the positive control of a tubulin gene in all samples. Panels C, F and I: Western blots using anti-FPLP antibody showed the presence of PFLP at 17 and 19 KDa bands (arrowheads), and extra signals at 22-24 KDa (star) in leaf extracts of AtCPFLP and AtESPFLP *Arabidopsis* lines. The proteins were probed with anti-PFLP antiserum. The numbers at the bottom indicate folds of fluorescence intensity as compare to the non-transgenic Col-0 plants.

The present invention relates to plant ferredoxin-like protein (PFLP), a photosynthetic type ferredoxin that is associated with the production of active oxygen species and hypersensitive reaction in plants. As ferredoxin is a protein mediating electron transfer in a range of metabolic reactions, such as those taking place in plant chloroplasts, it was believed that PFLP's function requires chloroplast localization or at least an intracellular localization. Indeed, PFLP contains a signal-peptide at its N-terminal region for targeting to chloroplasts.

Unexpectedly, as will be disclosed below, PFLP induces diseases resistance without being in a chloroplast localization or even inside a cell. This invention is based, at least in part, on this unexpected discovery.

PFLP-dependent disease defense might be mediated by harpin triggered hypersensitive response (HR). The HR is an effective mechanism associated with plant disease resistance during pathogens infection (Mehdy, 1994, *Plant Physiol.* 105:467-472). Harpin is an elicitor protein exported by type III pathway of plant pathogenic *Erwinia, Pseudomonas, Xanthomonas* spp. and *Ralstonia* spp. (Chen et al., 2008, *Phytopathol.* 98:781-791). Moreover, bacterial harpins are able to trigger plant defense responses (Chen et al., 2008, *Phytopathol.* 98 (7):792-802; Degrave et al., 2008, *Mol. Plant-Microbe Interact.* 21:1076-1086). The HrpZ encoded by hrpZ gene which is a harpin from *Pseudomonas syringae* pv. *syringae* can elicit HR in tobacco plants (He et al., 1993, *Cell* 73:1255-1266). In pflp-transgenic tobacco plants, PFLP can further enhance the HrpZ-mediated HR (Dayakar et al., 2003, *Plant Mol. Biol.* 51:913-924). In pflp-transgenic tobacco suspension cells, reactive oxygen species (ROS) generation is respond to HrpZ and dependent on membrane bound NADPH oxidase.

As shown below in the example, three different versions of PFLP: a PFLP lacking csp (d-pflp), an extracellularly secreted PFLP (es-pflp), and a chloroplast-targeting PFLP (cp-pflp) were expressed in transgenic *Arabidopsis* plants. They were targeted to different cellular compartments in the cells of the plants. It was found that transgenic *Arabidopsis* plants having d-pflp and es-pflp, but not that with cp-pflp, showed disease resistance against *R. solanacearum* strains, and the disease resistance of the transgenic plants are also correlated with the harpin-mediated HR. Most importantly, higher disease resistance was found when PFLP was outside the chloroplast, not inside.

The invention provides nucleic acids and polypeptides, such as es-pflp, that render plants enhanced disease resistance against bacterial pathogens. In particular, the nucleic acids can be used to generate transgenic plants.

Polypeptides of this invention include functional variants or functional equivalents of the above-described es-pflp, e.g., SEQ ID NO: 8. A functional equivalent of SEQ ID NO: 8 refers to a polypeptide derived from SEQ ID NO: 8, e.g., a fusion polypeptide or a polypeptide having one or more point mutations, insertions, deletions, truncations, or a combination thereof. It is at least 70% (e.g., 75%, 80%, 85%, 90%, 95%, 99%, or 100%) identical to SEQ ID NO: 8. The variants include biologically active fragments whose sequences differ from the es-pflp described herein by one or more conservative amino acid substitutions or by one or more non-conservative amino acid substitutions, deletions, or insertions that do not abolish the activity. All of the functional equivalents have substantially the es-pflp activity, i.e., the ability to render a plant resistant to a bacterial pathogen. This activity can be determined by the assays described in the examples below or any analogous assays.

The amino acid composition of a polypeptide of the invention may vary without disrupting its activity. For example, such a variant can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide is preferably replaced with another amino acid residue from the same side chain family. Alternatively, mutations can be introduced randomly along all or part of a polypeptide of this invention, such as by saturation mutagenesis, and the resultant mutants can be screened for the activity to identify variants of this invention.

A nucleic acid construct of the present invention can be transformed into a plant cell to produce a desired transgenic plant or plant cell. Methods for transforming plant cells with nucleic acid are routine in the art. Further, the plant cells can be transformed with multiple constructs, e.g., sequentially or concurrently. Depending on the desired physiological and agronomic properties of a plant species, and the nucleic acid construct of the present invention, a target plant or plant cell for transformation can include a species from maize, wheat, rice, soybean, tomato, broccoli, tobacco, sweet pepper, calla lily, orchid, carrots, peanut, potato, sugar beets, sunflower, yam, *Arabidopsis*, rape seed, sunflower, and petunia.

One implementation of the current invention utilizes *Agrobacterium* to introduce the desired construct into plant cells in the manner descried in, e.g., U.S. Pat. Nos. 5,177,010, 5,104,310, 5,149,645, 5,469,976, 5,464,763, 4,940,838, 4,693,976, 5,591,616, 5,231,019, 5,463,174, 4,762,785, 5,004,863, and 5,159,135; and European Patent Applications 116718, 290799, 320500, 604662, 627752, 0267159, and 0292435). The method can be used with both dicotyledonous plants cells (Bevan et al. (1982) *Ann. Rev. Genet.* 16:357-384; Rogers et al. (1986) *Methods Enzymol.* 118:627-641), and monocotyledonous plant cells. (Hernaisteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40.; Gould et al. (1991) *Plant Physiol.* 95:426-434). The method can employ binary *Agrobacterium* T-DNA vectors (Hoekema et al. (1983) *Nature* 03:179; Bevan, 1984, *Nuc. Acid Res.* 12:8711-8721), and the co-cultivation procedure (Horsch et al., 1985, *Science* 227:1229-1231).

Additional steps may be required to prepare a desired nucleic acid sequence for plant transformation. For example, in order to utilize T-DNA mediated transformation, the thionin coding sequence, operably linked to a heterologous promoter, is ligated into a binary vector, between the left and right border sequences of T-DNA. The binary vector can further include a gene encoding a selective marker, e.g., an Hph gene coding for hygromycin resistance. The binary vector containing the desired construction is transformed into an *E. coli* strain, e.g., DH5a. Subsequently, the binary plasmid is transferred into an *Agrobacterium*, e.g., *Agrobacterium* strain LBA4404, using a tri-parental mating.

Other methods for transforming plant cells are available. Of particular utility for transforming monocotyledonous plants or plant cells are methods of protoplast transformation which include, but are not limited to, protoplast transformation through calcium-, polyethylene glycol (PEG)- or electroporation-mediated uptake of naked DNA (see Paszkowski et al., 1984, *EMBO J* 3:2717-2722, Potrykus et al. 1985, *Molec. Gen. Genet.* 199:169-177; Fromm et al., 1985, Proc. Nat. Acad. Sci. USA 82:5824-5828; Shimamoto, 1989, *Nature* 338:274-276), microinjection, silicon carbide mediated DNA uptake (Kaeppler et al., 1990, *Plant Cell Reporter* 9:415-418), and microprojectile bombardment (see Klein et al., 1988, *Proc. Nat. Acad. Sci. USA* 85:4305-4309; Gordon-Kamm et al., 1990, *Plant Cell* 2:603-618), whiskers technology (see U.S. Pat. Nos. 5,302,523 and 5,464,765), and viral vector systems (see, U.S. Pat. Nos. 5,316,931, 5,589,367, 5,811,653, and 5,866,785). A transformed plant or transformed plant tissue can be assayed for resistance to pathogens.

The above-described polypeptides, e.g., es-pflp, d-pflp, and cp-pflp, can be formulated as a composition which is applied to plants in order to confer pathogen resistance. The composition can be prepared in a solution, e.g., an aqueous solution, at a concentration from about 0.005% to 10%, or about 0.01% to 1%, or about 0.1% to 0.5% by weight of polypeptide content. The solution can comprise an organic solvent, e.g., glycerol or ethanol. Alternatively, the composition can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include a stabilizer, spreading agent, wetting extenders, dispersing agents, sticking agents, disintegrators, and other additives, and can be prepared as a liquid, a water-soluble solid (e.g., tablet, powder or granule), or a paste. The composition can also include other desirable compounds, e.g., protease inhibitors, endotoxins, and the like.

Prior to application, the composition can be combined with another desired composition such an insecticide, germicide, fertilizer, plant growth regulator and the like. The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the composition can be applied to plant tissue from a volatile or airborne source. The source is placed in the vicinity of the plant tissue and the composition is dispersed by diffusion through the atmosphere. The source and the plant tissue to be contacted can be enclosed in an incubator, growth chamber, or greenhouse, or can be in sufficient proximity that they can outdoors.

In another implementation, if the composition is distributed systemically thorough the plant, the composition can be applied to tissues other than the leaves, e.g., to the stems or roots. Thus, the composition can be distributed by irrigation. The composition can also be injected directly into roots or stems.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example 1

Materials and Methods

Plants and Bacteria Growth Condition

Arabidopsis thaliana ecotype Columbia plants were planted in sterilized soil and grown in a growth chamber at 22° C. (16 hour light/8 hour dark). The Arabidopsis plants of 4-5 week-old were then used for Agrobacteria inoculation. Escherichia coli DH5α and A. tumefaciens GV3101 were grown in Luria-Bertani (LB) broth or on LB agar plates at 37° C. Antibiotics were used for selection at the following concentrations: 50 µg/mL of kanamycin for recombinant plasmids in E. coli, and gentamycin for A. tumefaciens. All strains of R. solanacearum were cultured at 28° C. for 48 hours on a TZC medium containing 1% dextrose, 1% peptone, 0.1% casein hydrolysate, and 0.1% 2,3,5-triphenyl tetrazolium chloride (Kelman 1954, Phytopathology 44:693-695).

Construction of the Transformation Plasmids

One recombinant plasmid pBI-DPFLP (FIG. 1A), harboring a d-pflp DNA fragment in pBI121 (Clontech, U.S.A.), was described in Huang et al., 2006, Plant Sci. 171:17-23. In order to make a replacement for the signal peptide of pflp, the pBI-D-PFLP was used for further construction. The coding sequence of the d-pflp DNA fragment was amplified from pBI-DPFLP by polymerase chain reaction (PCR) with the following primers: LS-ap1-sBamHI-F, 5'-CGCGGATC-CGCGCATGGCTTCATACAAAGTG-3' (SEQ ID NO:13) and LS-ap1-SacI-R, 5'-CCATCGGGCTTATGAGATCA-GAGCTC-3' (SEQ ID NO:14). PCR was carried out under the following conditions: 94° C., 10 minutes for initial denaturation; followed by 30 cycles of 94° C., 1 minute; 60° C., 45 seconds; and 72° C., 1 minute with 72° C., 10 minutes for final extension. The PCR product was digested with BamHI and SacI and purified after agarose gel electrophoresis. The PCR product was digested with BamHI and SacI, and purified from the gel after ImpactVector™1.2 Secreted expression and 1.4 Chloroplast expression (Wageningen UR, Netherlands) harbouring a chloroplast signal peptide (csp) from chrysanthemum and an extracellular secretion signal peptide (esp) from sea anemone (Outchkourov et al., 2003, Plant Physiol. 133: 379-390;
Outchkourov et al., 2003, Planta 216:1003-1012), respectively. Two constructions were performed by in-frame fusion of d-pflp fragment to the csp and esp to generate a cp-pflp and es-pflp fragment in recombinant plasmids pIVC-PFLP and pIVES-PFLP.

The cp-pflp DNA fragment was then amplified with the following primers: LS-ap1-CP-XbaI-F, 5'-TCTAGAATG-GCCTCGATCTC-3' (SEQ ID NO:15) and LS-ap1-SacI-R. The PCR product was digested with XbaI and SacI, and the cp-pflp DNA fragment was inserted into pBI121 to generate the plasmid pBI-CPFLP (FIG. 1D). Similarly, the es-pflp DNA fragment was amplified with the primer LS-ap1-ES-XbaI-F, 5'-TCTAGAAACCATGTCTCTTAGCCAGAAC-3' (SEQ ID NO:16) and LS-ap1-SacI-R. The es-pflp DNA fragment was constructed into pBI121 to generate the plasmid pBI-ESPFLP (FIG. 1G). These three plasmid vectors, pBI-DPFLP, pBICPFLP and pBI-ESPFLP, were transformed into A. tumefaciens GV3101. The inserted fragments of d-pflp, cp-pflp and es-pflp were sequenced and compared to the sequences on Genebank (AF039662).

Generation and Selection of Transgenic Arabidopsis

Transformation of Arabidopsis thaliana ecotype Columbia (Col-0) was performed using Agrobacterium tumefaciens containing the recombinant plasmid pBI-DPFLP, pBI-CPFLP and pBI-ESPFLP described above. The nptII gene in the vector allows the kanamycin selection of transgenic plants. Transgenic seeds were screened according to a rapid screening method for transgenic Arabidopsis seeds (Harrison et al., 2006, Plant Methods 2:19) on 1/2 Murashige and Skoogs medium (1/2 MS) containing kanamycin. Seedlings were then transplanted in the pots containing sterilized soil. The $T_1$ transgenic lines were confirmed by PCR with a forward primer for 35S (Huang et al., 2007, Phytopathol. 97:900-906), and a reverse primer PBI-IndR (5'-CCCAGTCAC-GACGTTGTAAA-3'(SEQ ID NO:17)). Individual $T_2$ plants from each line were self-pollinated, and seeds collected. $T_3$ transgenic plants were identified with PCR to define whether $T_2$ transgenic plant is a homozygous line.

Molecular Characterizations of Transgenic Arabidopsis Lines

Genomic DNA was isolated from leaf tissue of each transgenic Arabidopsis $T_1$ plant using a plant genomic DNA purification kit (Geneaid, Taiwan). The coding sequence of d-pflp, cp-pflp and es-pflp were amplified by PCR in the manner described above using with a 35S and PBI-IndR. Total RNA was isolated from fresh leaf tissue of four-week-old tobacco plants using a plant total RNA kit (Viogene, Taiwan). For RT-PCR analysis, first-strand cDNA was synthesized using $1^{st}$ Strand cDNA synthesis Kit for RT-PCR [AMV] (Roche, Germany) from 1 µg of total RNA, and 10 of the cDNA was subjected to PCR in a 20 µl reaction volume with primers LS-ap1-RTF (5'-CACACCTGACGGAC-CAAT-3'(SEQ ID NO:18)) and LS-ap1-RTR (5'-CGAGT-TCTGCTTCTTTGTG-3' (SEQ ID NO:19)). The tubulin gene was used as a positive control using primers Tub2AF and Tub2AR (Lee et al., 2000, Arabidopsis. Genes Dev. 14:2366-2376). The subsequent PCR amplification used the same conditions described above, and the RT-PCR products were analyzed by electrophoresis on a 1.5% agarose gel. For Western-blot analysis, the total protein was extracted from four-week-old leaf tissues. The tissue (100 mg) was homogenized with a steel ball in 500 µL of an extraction buffer (100 mM NaCl, 50 mM Tris-HCl and 1 mM PMSF at pH7.5), and the amount of total protein was quantified with a BCA protein assay kit (Thermo, U.S.A.). Protein extracts at 3 µg of total protein were fractionated on 15% SDS-polyacrylamide gels, and the separated proteins were then transferred to Immobilon-P PVDF membrane (Millipore, USA). Western blot was performed using a rabbit polyclonal antiserum specific for the PFLP protein as primary antibody (1:2000) and HRP-conjugated goat anti-rabbit IgG (Rockland, USA) as secondary antibody.

Disease Severity Assay

A disease soil method was used to evaluate wilt symptom on Col-0 plants after inoculation with four *R. solanacearum* strains isolated from radishes (Rd4 and Rd15) and tomatoes (Ps95 and Ps152). Four-week old *Arabidopsis* (each plant had eight leaves) were grown in growth chambers at 25° C. for disease severity assay of bacterial wilt disease. The colony of each *R. solanacearum* strain tested in this study was picked and enriched on a TZC basal medium for 48 hours at 28° C., and then the cells were washed from plates in distill water and adjusted the bacterial suspension to $OD_{600}$ of 0.3. The bacterial suspension of each *R. solanacearum* strain was mixed with 10-folds volume of soil mixture for disease soil preparation. *Arabidopsis* plants were then planted in pots containing disease soil, and the wilt symptoms were recorded for four weeks after inoculation. Disease index of wilt disease on *Arabidopsis* was exhibited by weeks post-inoculation and rated the scales from 0 to 6 (0: no wilting, 1: one to two leaves wilting; 2, three to four leaves wilting, 3: five to six leaves wilting, 4: seven to eight leaves wilting, 5: over nine leaves wilting, 6: death). And, then the numbers of plants with different scales of wilt disease were obtained as $N_0$-$N_6$. Disease index for each trial was calculated by the following formula: $[(0 \times N_0 + 1 \times N_1 + 2 \times N_2 + 3 \times N_3 + 4 \times N_4 + 5 \times N_5 + 6 \times N_6)/(6 \times N)] \times 100\%$ (Winstead et al., 1952, *Pseudomonas solanacearum. Phytopathology* 42:628-634). In this assay, twelve *Arabidopsis* plants were tested of each *R. solanacearum* strain or each transgenic line.

Confocal Microscopy

Localization of PFLP expressed in transgenic plants was performed by confocal laser microscopy observation as described (Padham et al., 2007, *Arabidopsis. Plant Physiol.* 143:1372-1384). Leaves were cut from 3-4 week-old *Arabidopsis* plants, and the leaf strips (2 mm width) were soaked for 2 hr in 50% ethanol at 4° C., washed for 30 min with phosphate buffered saline (PBS) twice at room temperature, treated with 1% Cellulase R10 (Yakult, Japan) for 1 hr and followed by 1% Triton X-100 in PBS at room temperature for 1 hr to permeabilize the tissue. For immuno-staining, of leaf strips were then gently shaken overnight at room temperature in the presence of the primary antibody (1:50) in PBS containing 1% bovine serum albumin (BSA). After leaf strips were washed twice in PBS, strips were probed with FITC-conjugated goat anti-rabbit antibody (KPL, USA; 1:80 in PBS containing 1% BSA) for 2 h in the dark at room temperature. Leaf strips were washed twice with PBS and placed on slides for observation under a Zeiss LSM 510 confocal laser-scanning microscope.

HrpZ Preparation and HR Assay

A recombinant plasmid pSY10 harbouring the hrpZ gene (HrpZ) was maintained in *Escherichia coli* DH5α. Protein extraction and infiltration of HrpZ were carried out as described in Ger et al., 2002, *Mol. Plant-Microbe Interact.* 15:764-773. *E. coli* strain was cultured overnight in LB broth containing ampicillin (50 μg/ml) at 37° C. with shaking in the presence of isopropylthio-β-D-galactoside. To obtain HrpZ, the bacteria were washed and sonicated in a 25 mM phosphate buffer (pH 7.5) for 30 seconds, and then boiled for 10 minutes. After boiling, the protein extracts were centrifuged at 10,000×g for 10 minutes, and the supernatants were stored at 4° C. *Arabidopsis* leaves were punctured with a 25-gauge needle to form tiny holes on the leaf surface and the then infiltrated with HrpZ by pressing a 1 ml blunt syringe through the holes. For ROS observation, leaves were cut and further infiltrated with 5 mM 3,3'-diaminobenzindine (DAB) at pH3.8 by vacuum for 20 minutes, and then incubated at room temperature for 4 hours. Chlorophyll was removed with ethanol immersion followed by boiling the leaves in water for 10 minutes. The brown product was detected after reactions of DAB, indicating the $H_2O_2$ accumulation (Fryer et al., 2002, *J. Exp. Botany* 53:1249-1254). After infiltrating for over 24 hours, HR necrosis could also be observed. We calculated the HR ratio in percentage by observation of the ratio of necrosis appeared around six inoculation sites in three independent leaves of one plant, and ten plants of transgenic *Arabidopsis* lines were tested for replicates in this assay.

Results

Characterization of Transgenic Lines

To analyze where PFLP functions in *Arabidopsis* cells to enhance disease resistance, we constructed three different versions of PFLP in pBI121-derived recombinant plasmid, the pflp gene with signal peptide deleted (d-pflp), with signal peptide replaced with chloroplast targeting peptide (cp-pflp), and with signal peptide replaced an extracellular secreted peptide (es-pflp) (FIG. 1). Each construct was then transformed into individual *Arabidopsis* by *Agrobacterium*-mediated transformation to generate transgenic *Arabidopsis* plants, AtDPFLP, AtCPFLP and AtESPFLP. No apparent morphological differences were observed between transgenic and non-transgenic plants. AtDPFLP (#1-8 and #6-7), AtCP-FLP (#2-1 and #11-3) and AtESPFLP (#1-19 and #2-9) transgenic lines were selected to detect the presence of d-pflp, cp-pflp or es-pflp transcripts by RT-PCR, respectively (FIG. 1 B, E, H). Neither recombinant DNA nor its transcripts of d-pflp, cp-pflp or es pflp were detected in non-transgenic *Arabidopsis* plant (Col-0).

Protein from leaves of $T_2$ transgenic plants and Col-0 plant were then extracted and probed with anti-PFLP antibody by Western blot. In Col-0 plants, two endogenous ferredoxin isoproteins with 17 and 19 KDa respectively were detected by PFLP antibody. In all selected transgenic plants, the same immunological signals at 17 and 19 KDa were also detected, with intensities increased by 157% in AtDPFLP line #1-8, 185% in AtDPFLP line #6-7, 159% in AtCPFLP line #2-1, 148% in AtCPFLP line #11-3, 170% in AtESPLP line #1-19, and 189% in AtESPLP line #2-7, when compared to the signal from Col-0 plants (FIG. 1 C, F, I). Two additional signals at 23 and 24 KDa translated from cp-pflp were also detected in AtCPFLP lines #2-1 and #11-3 (FIG. 1F), and one extra immunological signal at 22 KDa translated from es-pflp was detected in both AtESPFLP lines #1-19 and #2-7 (FIG. 1I). These results demonstrated that engineered d-pflp, cp-pflp and es-pflp genes were all successfully expressed in the $T_2$ generation of these transgenic *Arabidopsis* plants. The mRNA and protein of d-pflp, cp-pflp and es-pflp genes were also detected in $T_3$ transgenic *Arabidopsis* plants.

Immuno-Localization of PFLP

We examined the localization of PFLP in different cellular compartments with FITC-conjugated antibodies which recognized PFLP. Immuno-localization of PFLP in the leaves of transgenic *Arabidopsis* plants was observed by confocal laser microscopy. Images were obtained from five-week-old plants. We found in the cells of Col-0 plants) (as control materials), the FITC signals in the chloroplast were weak, indicating that the endogenous ferredoxins in the chloroplast could be detected by PFLP antibody. In the cells of AtDPFLP plants, the FITC signals appeared outside the chloroplasts besides the endogenous signals. The result indicated that PFLP was existed in the cytoplasm. In the AtCPFLP cells, the FITC fluorescent images superimposed on the chlorophyll autofluorescence were stronger than that in Col-0 plant, indicating that the PFLP was localized in the chloroplasts. In AtESPFLP plants, obvious FITC signals were detected in the extracellular space, indicating that the PFLP was secreted outside the cells. These results demonstrated that the engineered PFLP targeted to designated cellular compartments.

Bacterial Wilt Disease on *Arabidopsis* Plants

To evaluate the efficacy of engineered PFLP against bacterial wilt diseases on *Arabidopsis*, a bioassay system was developed. When *Arabidopsis* was inoculated with *R. solanacearum*, bacterial wilt disease would appear two weeks post inoculation (wpi). Four different strains, Rd4, Rd15, Ps95 and Ps152, to Col-0 and all AtDPFLP, AtCPFLP and AtESPFLP transgenic plants were inoculated, and then the numbers of plants with bacterial wilt symptoms during 4 wpi were obtained. The disease index was then calculated by dividing the number of wilting leaves to total inoculated plants. The higher the index, the less resistant the plants have against the bacterial pathogens.

Figure 2:
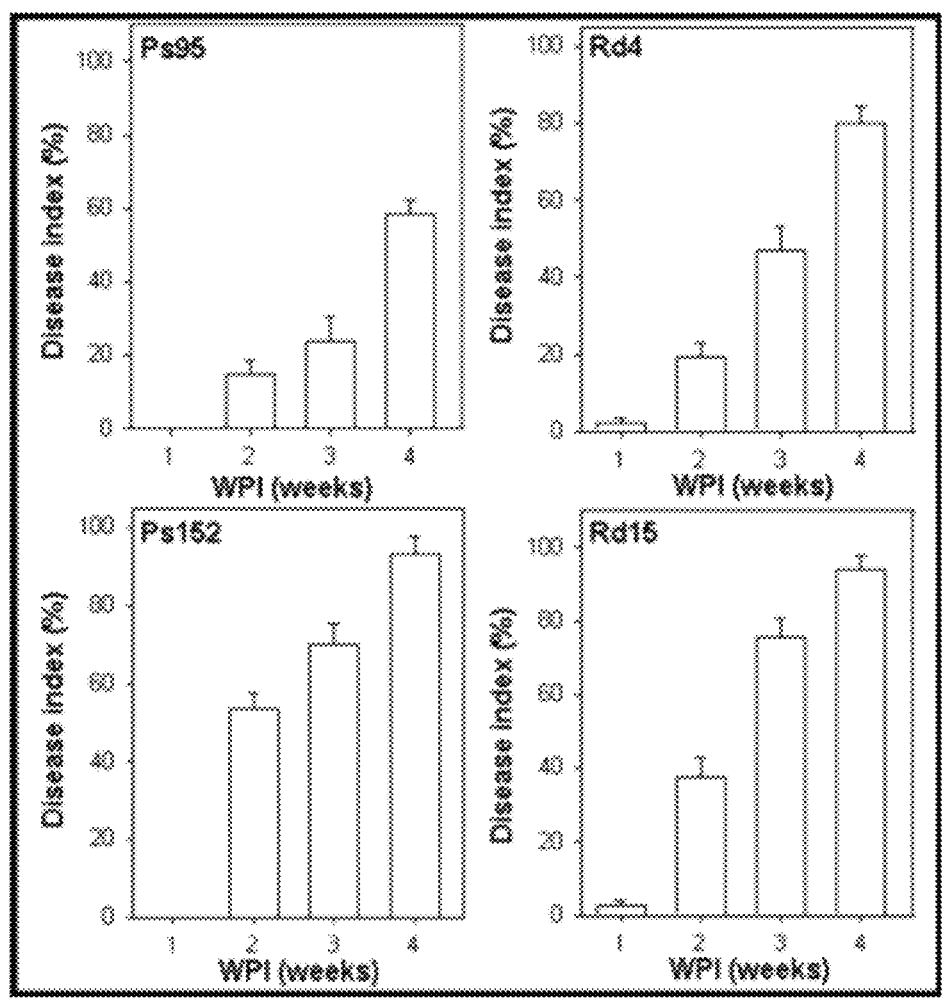
FIG. 2 is a set of bar graphs showing results from Col-0 *Arabidopsis* plants. Four-week-old plants were transplanted into soil prepared by mixing with bacterial suspension of different *R. solanacearum* strains (Ps95, Rd4, Ps152 and Rd15). The graphs show the progressive changes of disease indexes by weekly. Error bars indicate standard deviation of the mean of twelve individual plants. Distilled water was used as the negative control (Con) in these experiments.
Figure 3:
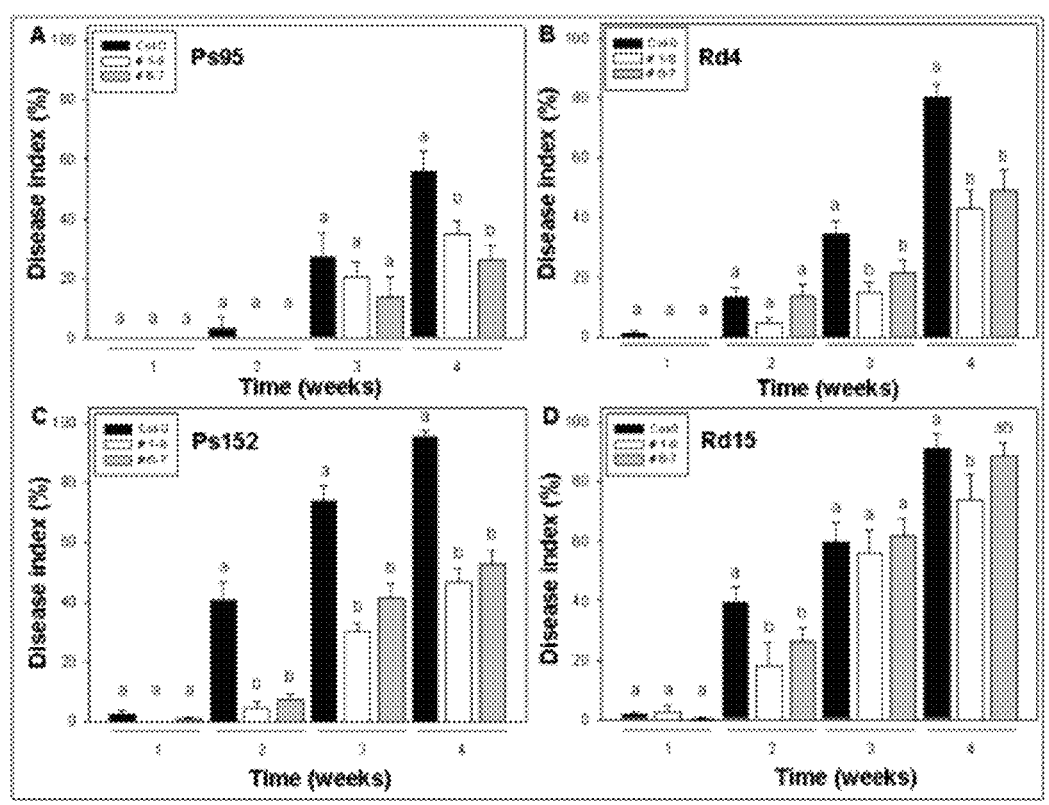
FIG. 3 is a set of bar graphs showing results from AtDPFLP transgenic *Arabidopsis* plants. Four-week old *Arabidopsis* plants were inoculated with different *R. solanacearum* strains (Ps95, Rd4, Ps152 and Rd15). Disease indexes were monitored as described in FIG. 2. Error bars indicate standard deviation of the mean for twelve individual plants inoculated by each strain. Letters in the figures indicate the significant differences based on the Duncan's multiple range test (P<0.05).

The disease index on Col-0 wild type plants was examined first. After having inoculated Rd4, Rd15 and Ps152 on Col-0 plants, we obtained the disease index of 80.1%, 93.9% and 93.3%, respectively at 4 wpi. However, we observed a slower development of disease caused by Ps95 and also calculated a lower disease index 58.5% at 4 wpi (FIG. 2). We then challenged the transgenic plants, and observed that the developments of wilt symptom caused by these strains tested were varied. Four-week-old plants were transplanted into soil prepared by mixing with the bacterial suspension. We compared two strains, Rd4 and Rd15, and found that both of these two strains could cause whole plant death at 4 wpi. Rd15 caused wilt symptom on non-transgenic Col-0 plant at 2 wpi and plant death rapidly. Then, we obtained the disease indexes of two $T_3$ AtDPFLP transgenic plants, #1-8 and #6-7, which retain PFLP in the cytoplasm. When these lines were inoculated with Ps95, the disease indexes were 34.8%, 26.2% at 4 wpi, respectively, which were lower than that of Col-0 wild type plants (56.1%) (FIG. 3 A). The disease indexes caused by Rd4 and Ps152 were around 20% at 2 wpi which was lower than that of Col-0 40% to 60% at 2 wpi. At 4 wpi, the disease indexes of AtDPFLP #1-8 and #6-7 lines were only approximately half (43.1% to 52.6%) of those in Col-0 plants (81.0% to 95.2%) (FIG. 3 B, C). These results demonstrated the resistance of AtDPFLP lines was sustained upon challenges by these three *R. solanacearum* strains Rd4, PS95 and Ps152. However, AtDPFLP lines only exhibited resistance in the first two weeks after inoculation of strain Rd15 (#1-8, 19.5%; #6-7, 26.3%; and Col-0, 39.2% at 2 wpi), and then the wilt symptom developed in the following two weeks rapidly (#1-8, 76.4%; #6-7, 90.2%; and Col-0, 95.1% at 4 wpi) (FIG. 3 D). Rd15 could cause lethality to AtDPFLP and Col-0 plants at 4 wpi.

Figure 4:
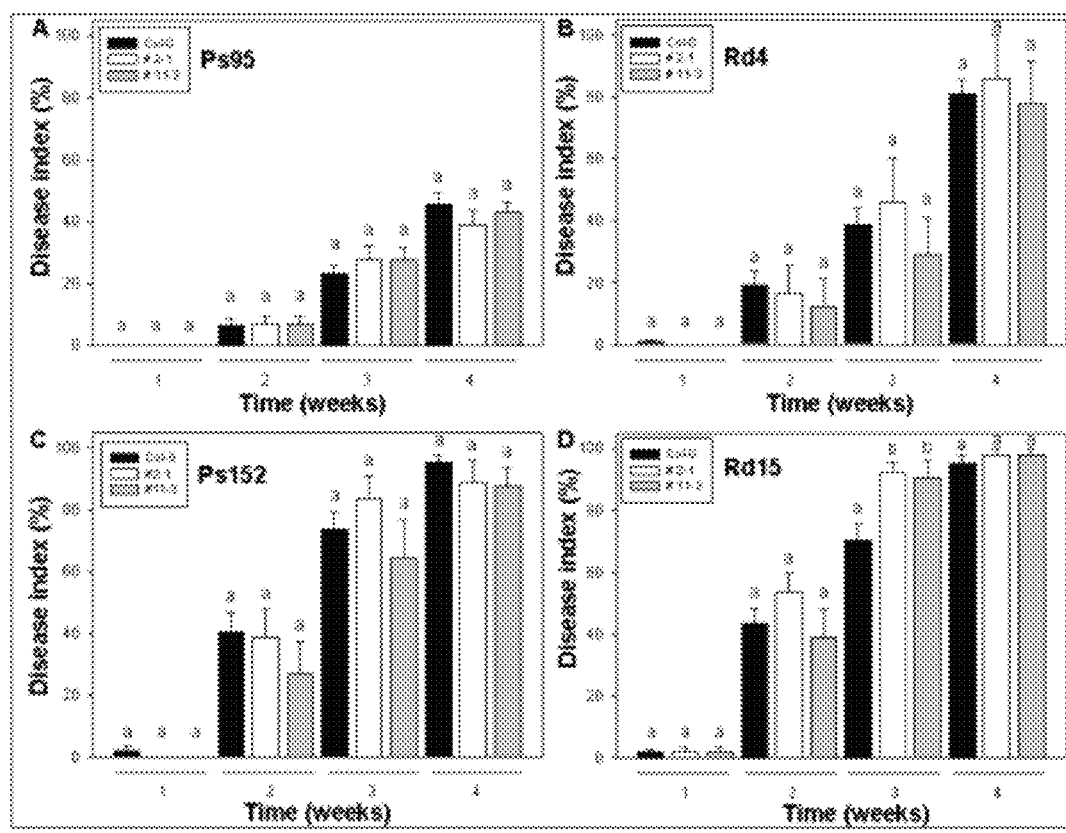
FIG. 4 is a set of bar graphs showing results from AtCPFLP transgenic *Arabidopsis* plants. Four-week old *Arabidopsis* plants were inoculated with different *R. solanacearum* strains (Ps95, Rd4, Ps152 and Rd15) were monitored as described in FIG. 2. White bars represent line #2-1, gray bars represent line #11-3, and black bars represent the Col-0. Error bars indicate standard deviation of the mean for twelve individual plants inoculated by each strain. Letters in the figures indicate the significant differences based on the Duncan's multiple range test (P<0.05).

In contrast, the two AtCPFLP $T_3$ plants #2-1 and #11-3 which import PFLP to the chloroplast did not show lower disease indexes when compared to Col-0 plants: caused by Ps95, #2-1, 38.9% and 11-3, 43.0% (FIG. 4 A); by Rd4, #2-1, 86.1% and #11-3, 77.8% (FIG. 4 B); by Ps152, #2-1, 88.9% and #11-3, 87.5% (FIG. 4 C); and by Rd15, #2-1, 98.1% and #11-3, 98.1% (FIG. 4 D). Notably, the wilt symptoms on transgenic AtCPFLP plants caused by Rd4 or Rd15 developed as rapidly as those on Col-0 plants at 4 wpi.

Figure 5:
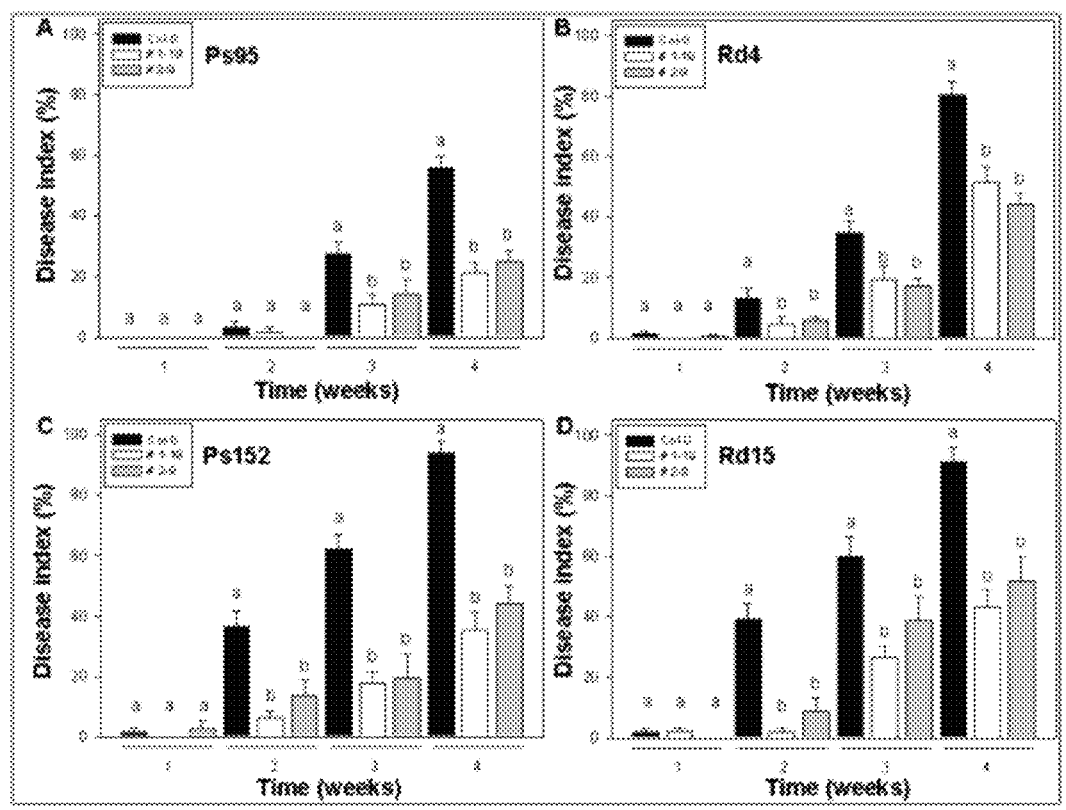
FIG. 5 is a set of bar graphs showing results from AtESPFLP transgenic *Arabidopsis* plants. Four-week old *Arabidopsis* plants were inoculated with different *R. solanacearum* strains (Ps95, Rd4, Ps152 and Rd15) and the progressive changes in bacterial wilt symptom were monitored as described in FIG. 2. White bars represent line #1-19, gray bars represent line #2-9, and black bars represent the Col-0. Error bars indicate standard deviation of the mean for twelve individual plants inoculated by each strain. Letters in the figures indicate the significant differences based on the Duncan's multiple range test (P<0.05).

We then test if PFLP is functioning as a secreted protein in the transgenic AtESPFLP $T_3$ plants (#1-19 and #2-9) which are transformed with es-pflp. It was found that both AtESP-FLP plants had lower diseases indexes compared to those of Col-0 plants at 4 wpi, caused by Ps95, #1-19, 21.2% and #2-9, 25.0% (FIG. 5 A); by Rd4, #1-19, 51.5% and #2-9, 43.9% (FIG. 5 B); by Ps152, #1-19, 35.4% and 2-9, 44.4% (FIG. 5 C); and by Rd15 #1-19, 43.3%; #2-9, 50.0% (FIG. 5 D). These results indicated the AtESPFLP plants that secreted PFLP to extracellular matrix had strong resistance against bacterial wilt pathogens.

Hypersensitive Response Induced by HrpZ in Transgenic Plants

Figure 6:
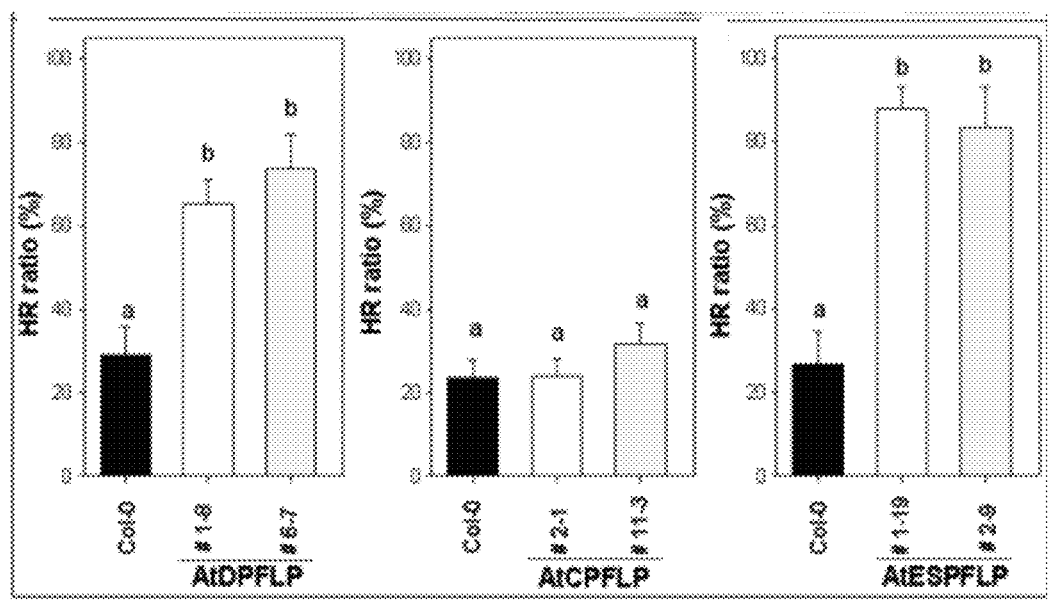
FIG. 6 is a set of bar graphs and photographs showing results of HrpZ-mediated hypersensitive response (HR) in leaves of transgenic and wild-type *Arabidopsis*. The HrpZ recombinant protein prepared from *E. coli* was infiltrated into the leaves of transgenic *Arabidopsis*. HR necrosis was observed after 24 hr post-inoculation and the HR ratio were calculated for each line of the plants.

Disease resistance against pathogens can be activated by harpin-mediated HR, and this effect was intensified in pflp-transgenic tobacco plants. The effects of different targeting PFLP in pathogen resistance can thus be measured by the degree of HR induced by HrpZ. We infiltrated the wild type Col-0 plants and the AtDPFLP, AtESPFLP and AtCPFLP transgenic plants with HrpZ and calculated the HR ratio by measuring the level of $H_2O_2$ accumulation produced by NADPH oxidase. We first used DAB as substrates to trace the level of $H_2O_2$. We found that dark brown colored areas were displayed in the leaves of AtDPFLP and AtESPFLP plants while no obvious appearance could be detected in those of AtCPFLP and Col-0. These results showed the strong $H_2O_2$ accumulation in AtDPFLP and AtESPFLP plants, but not AtCPFLP and Col-0 plants. We then measured the HR ratio by counting the necrosis appeared around inoculation sites of the plant leaves. The HR ratios of AtDPFLP lines were 65.1% to 69.4%, and AtESPFLP lines were 82.1% to 80.9%, respectively, compared to those in the AtCPFLP lines (23.8% to 31.6%) and Col-0 (26.3%) at 24 hours after infiltration (FIG. 6). These results showed the HR was intensified in AtDPFLP and AtESPFLP plants, but not AtCPFLP and Col-0 plants.

The bacterial wilt disease, caused by *Ralstonia solanacearum*, is an important disease of many crops and other plants. The ecotype Col-0 was susceptible to strains Ps95, Rd4 and Rd 15. By employing the same rating procedure we found that the virulence of three strains of *R. solanacearum* were classified as strong virulent strains (Rd4, Rd15 and Ps152), and one (Ps95) was a weak strain. These four strains could be used to evaluate different levels of resistance obtained from transgene. The AtDPFLP and AtESPFLP transgenic lines described above were resistant to all of the four *R. solanacearum* strains tested. As PFLP also rendered resistance to bacterial soft rot caused by *E. carotovora* subsp. *carotovora* (Huang et al., 2006, *Plant Sci.* 171:17-23), it is expected that the above-described heterologous d-pflp or es-pflp gene could also protect plants against a wide spectrum of bacterial pathogens.

The PFLP-enhanced plant disease resistance is associated with harpin-mediated HR. HrpZ elicits ROS generation to induce HR in an NADPH-oxidase-dependent manner in pflp-transgenic tobacco plants. In *Arabidopsis*, this is not only evident in the case that the extracellular secreted PFLP in AtESPFLP plants was able to enhance HrpZ-mediated HR and increase disease resistance, but also in other case that neither HR nor disease resistance was enhanced in AtCPFLP plants. It was unexpected that AtESPFLP lines were more sensitive to HrpZ and had a higher resistance against the strong virulent strain Rd15 than AtDPFLP lines. Besides, the PFLP also exhibits antimicrobial activity against bacterial pathogen (Huang et al., 2006, *Plant Sci.* 171:17-23). We suggested the extracellular PFLP provided antibacterial activity and higher sensitivity response to bacterial elicitor would increase more disease resistance against bacterial pathogens than that of cytoplasmic PFLP.

In pflp-transgenic tobacco cells, PFLP exists in both chloroplasts and cytoplasm, no matter the transgene containing authentic signal peptide sequence or not (Dayakar et al., 2003, *Plant Mol. Biol.* 51:913-924; Huang et al., 2006, *Plant Sci.* 171:17-23), suggesting that the signal peptide of PFLP from pepper has low efficiency of chloroplast targeting in tobacco. Here we demonstrated that in pflp-Arabidopsis the PFLP with no signal peptide would exist in the cytoplasm. While the transgene contains the chloroplast targeting signal peptide (csp) of RbcS, the expressing PFLP could be delivered into chloroplasts effectively and faithfully in transgenic Arabidopsis plants. The RbcS precursor protein imports into chloroplast of pea followed by two-step cleavage. This explains why PFLP expressed in transgenic Arabidopsis plants with cp-pflp had two additional protein bands with 23 and 24 KDa, respectively (FIG. 1, F). When the signal peptide of PFLP was replaced by a typical eukaryotic-secreted signal peptide, the PFLP was observed in the extracellular space. The esp signal peptide sequence helps target protein for extracellular secretion through endoplasmic reticulum.

Leaf type ferredoxins are well known as electron transfer proteins in the photosynthetic system of chloroplast, and PFLP is similar to the leaf type ferredoxin. In addition, PFLP can enhance ROS generation and harpin-mediated HR. ROS generation is related to the membrane bound NADPH oxidase which is encoded by rboh gene. Here, the expression of PFLP outside the chloroplast did enhance disease resistance and intensify the harpin-mediated HR. Since PFLP can enhance resistance against bacterial pathogens, our study provides advanced evidence that it is only achieved while PFLP is outside the chloroplast. The ectopic PFLP outside the chloroplast does not process electron transfer in photosynthesis. Instead, it could be responsible for harpin-mediated ROS generation.

Example 2

Figure 7:
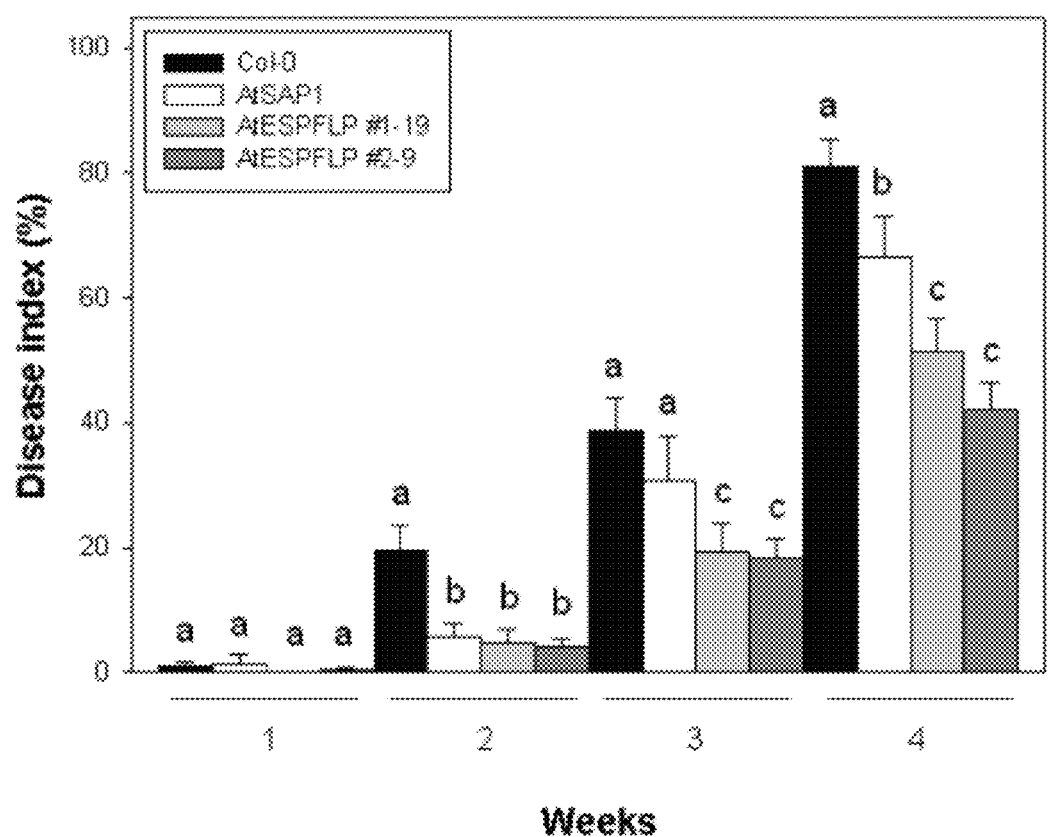
FIG. 7 is a graph showing disease index of *Arabidopsis thaliana* plants caused by *Ralstonia solanacearum* Rd4. Four-week-old *Arabidopsis* plants were transplanted into a soil that was prepared by mixing at 1:10 ratio (v/v) of bacterial suspension ($OD_{600}$~=0.3) of Rd4. White bars represent AtSAP1, gray and twilled gray bars represent AtESPFLP line #1 and #2, and black bars represent the Col-0. Error bars indicate standard deviation of the mean for twelve individual plants inoculated by each strain. Letters in the figures indicate the significant differences based on the Duncan's multiple range test (P<0.05).

In order to evaluate the effect of transgenic plants with ES-PFLP or PFLP on disease resistance, two transgenic plants AtESPFLP and AtSAP were challenged with bacterial wilt pathogen Ralstonia solanacearum Rd4. The AtSAP express PFLP with original signal peptide. The disease indexes of AtESPFLP (#1: 51.5%, #2: 42.2%) and AtSAP1 (66.7%) plants indicate that they were more resistance against R. solanacearum Rd4 than wild type (Col-0: 80.1%). Moreover, AtESPFLP plants showed 2.4-folds more resistance than AtSAP1 plants (FIG. 7).

Total protein from AtSAP1 (1.6 and 1.2) and AtESPFLP #1 (2.1 and 1.0) plants were extracted, and subject to Western Blot analysis in the same manner described above. The proteins were probed with anti-PFLP antiserum. Western blots showed the presence of PFLP as 17 and 19 KDa bands, and as an extra 22 KDa band in leaf extracts of AtESPFLP Arabidopsis lines. The results indicated that the averaged fd signals detected by Western blot were similar.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated polypeptide comprising
   a first segment that contains the sequence of SEQ ID NO: 5, and
   a second segment that contains an extracellular secretion signal having the sequence of SEQ ID NO:9.

2. The polypeptide of claim 1, wherein the polypeptide is derived from a plant.

3. The polypeptide of claim 2, wherein the plant is a cotton, pepper, tobacco, or tomato plant.

4. The polypeptide of claim 1, wherein the polypeptide comprises SEQ ID NO:7.

5. The polypeptide of claim 1, wherein the polypeptide enhances disease resistance of a plant against a bacterial pathogen.

6. The polypeptide of claim 5, wherein the plant is a cotton, pepper, tobacco, or tomato plant.

7. An isolated nucleic acid molecule comprising a sequence that encodes the polypeptide of claim 1.

8. The nucleic acid molecule of claim 7, wherein the sequence is the sequence of SEQ ID NO: 8.

9. A vector containing the nucleic acid molecule of claim 7.

10. A transformed host cell containing the nucleic acid molecule of claim 7.

11. A transgenic plant that expresses a polypeptide, wherein the polypeptide is the polypeptide of claim 1, and expression of the polypeptide in the transgenic plant enhances disease resistance of the plant against a bacterial pathogen in the transgenic plant, wherein the expressed polypeptide is secreted into the extracellular space.

12. A transgenic plant whose genomic DNA comprises the nucleic acid molecule of claim 7.

13. The transgenic plant of claim 11, wherein the bacterial pathogen is a pathogenic Gram-negative bacterium.

14. The vector of claim 9, wherein the nucleic acid molecule comprises the sequence of SEQ ID NO:8.

15. The transformed host cell of claim 10, wherein the nucleic acid molecule comprises the sequence of SEQ ID NO:8.

16. The transgenic plant of claim 12, wherein the nucleic acid molecule comprises the sequence of SEQ ID NO:8.

* * * * *